United States Patent
Sürth et al.

(10) Patent No.: US 9,545,516 B2
(45) Date of Patent: Jan. 17, 2017

(54) TRIPHASIC PULSES TO REDUCE UNDESIRABLE SIDE-EFFECTS IN COCHLEAR IMPLANTS

(71) Applicant: MED-EL Elektromedizinische Geraete GmbH, Innsbruck (AT)

(72) Inventors: Werner Sürth, Axams (AT); Reinhold Schatzer, Birgitz (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/976,131

(22) Filed: Dec. 21, 2015

(65) Prior Publication Data

US 2016/0106980 A1 Apr. 21, 2016

Related U.S. Application Data

(63) Continuation-in-part of application No. 14/334,743, filed on Jul. 18, 2014, now Pat. No. 9,265,944.

(60) Provisional application No. 61/856,090, filed on Jul. 19, 2013.

(51) Int. Cl.
*A61N 1/36* (2006.01)
*A61N 1/05* (2006.01)

(52) U.S. Cl.
CPC ......... *A61N 1/36032* (2013.01); *A61N 1/0541* (2013.01)

(58) Field of Classification Search
CPC .................................................. A61N 1/36032
See application file for complete search history.

(56) References Cited

U.S. PATENT DOCUMENTS

| 5,601,617 A * | 2/1997 | Loeb ................. A61N 1/36032 607/56 |
| 2007/0225767 A1* | 9/2007 | Daly ................. A61B 5/04001 607/2 |
| 2012/0130449 A1 | 5/2012 | Carlyon et al. |

(Continued)

OTHER PUBLICATIONS

International Searching Authority, International Search Report and Written Opinion—PCT/US2014/047123, date of mailing Dec. 5, 2014, 16 pages.

(Continued)

*Primary Examiner* — George Evanisko
(74) *Attorney, Agent, or Firm* — Sunstein Kann Murphy & Timbers LLP (57) ABSTRACT

An arrangement is described for generating electrode stimulation signals to electrode contacts in an implanted cochlear implant electrode array. A signal processor processes an input sound signal to generate stimulation timing signals for signal channels associated with the electrode contacts. A pulse generator produces the electrode stimulation signals for each electrode contact based on the stimulation timing signals. A pulse adapter controls a signal format of the pulse generator in response to a somatic response input signal reflecting presence or absence of an undesired somatic response to the electrode stimulation signals. The signal format is an initial signal format based on biphasic stimulation pulses when the somatic response input signal reflects absence of the undesired somatic response, and an adapted signal form based on triphasic stimulation pulses when the somatic response input signal reflects presence of the undesired somatic response.

24 Claims, 8 Drawing Sheets

(56) References Cited

U.S. PATENT DOCUMENTS

2012/0191161 A1    7/2012  van Dijk

OTHER PUBLICATIONS

MED EL Medical Electronics, "Sonata Ti100 Cochlear Implant Manual (online)", Med-El, Jan. 24, 2013, retrieved on Oct. 28, 2014 from the internet—http:www.medel.com/data/pdf20332E.pdf entire document, 20 pages.

Valero, et al, "Electrophysiologic and Behavioral Outcomes of Cochlear Implantation in Children with Auditory Nerve Hypoplasia", *Ear and Hearing*, vol. 32, No. 4, 0-0, 16 pages.

* cited by examiner

TRIPHASIC PULSES TO REDUCE UNDESIRABLE SIDE-EFFECTS IN COCHLEAR IMPLANTS

This application is a continuation in part of co-pending U.S. patent application Ser. No. 14/334,743, filed Jul. 18, 2014, which claims priority from U.S. Provisional Patent Application 61/856,090, filed Jul. 19, 2013, both of which are incorporated herein by reference in their entireties.

FIELD OF THE INVENTION

The present invention relates to hearing implant systems, and more specifically, to techniques for producing electrical stimulation signals in such systems.

BACKGROUND ART

Figure 1:
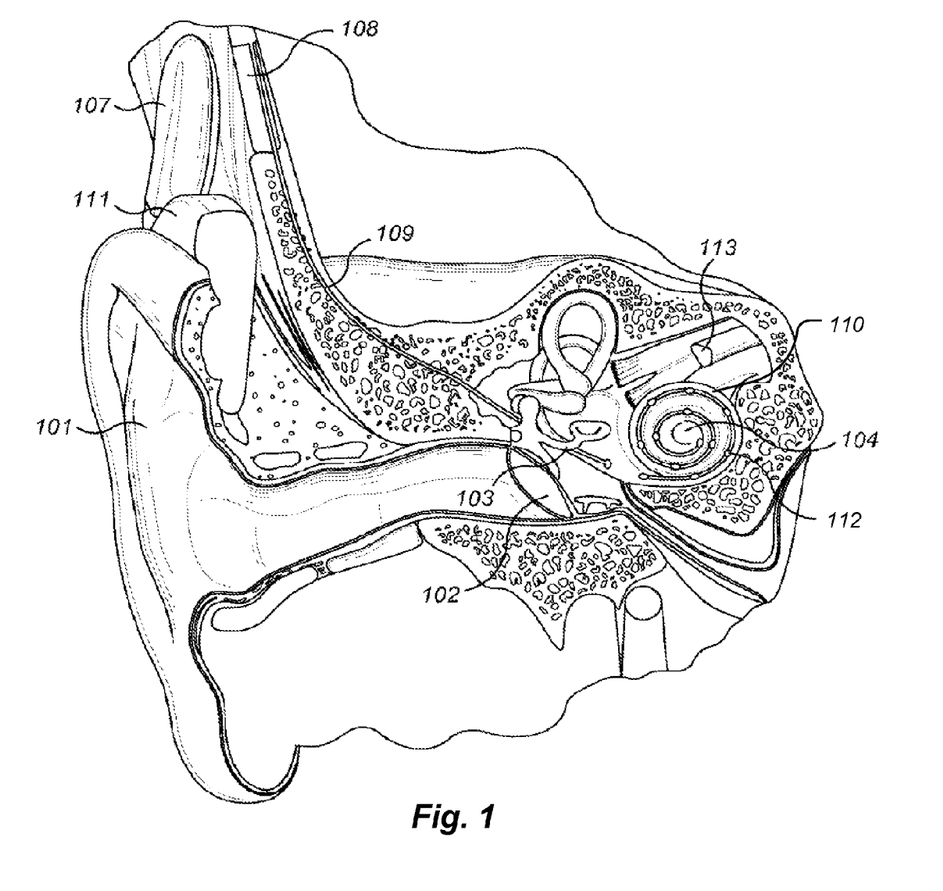
FIG. 1 shows anatomical structures in a human ear having a cochlear implant system.

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, the electrode array 110 includes multiple electrode contacts 112 on its surface that provide selective stimulation of the cochlea 104. Depending on context, the electrode contacts 112 are also referred to as electrode channels. In cochlear implants today, a relatively small number of electrode channels are each associated with relatively broad frequency bands, with each electrode contact 112 addressing a group of neurons with an electric stimulation pulse having a charge that is derived from the instantaneous amplitude of the signal envelope within that frequency band.

It is well-known in the field that electric stimulation at different locations within the cochlea produce different frequency percepts. The underlying mechanism in normal acoustic hearing is referred to as the tonotopic principle. In cochlear implant users, the tonotopic organization of the cochlea has been extensively investigated; for example, see Vermeire et al., *Neural tonotopy in cochlear implants: An evaluation in unilateral cochlear implant patients with unilateral deafness and tinnitus*, Hear Res, 245(1-2), 2008 Sep. 12 p. 98-106; and Schatzer et al., *Electric-acoustic pitch comparisons in single-sided-deaf cochlear implant users: Frequency-place functions and rate pitch*, Hear Res, 309, 2014 March, p. 26-35 (both of which are incorporated herein by reference in their entireties).

In some stimulation signal coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS), channel specific sampling sequences (CSSS) (as described in U.S. Pat. No. 6,348,070, incorporated herein by reference), spectral peak (SPEAK), and compressed analog (CA) processing.

In the CIS strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem).

In a CIS system, the stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 μs, which is near the lower limit.

The Fine Structure Processing (FSP) strategy by Med-El uses CIS in higher frequency channels, and uses fine structure information present in the band pass signals in the lower frequency, more apical electrode channels. In the FSP electrode channels, the zero crossings of the band pass filtered time signals are tracked, and at each negative to positive zero crossing, a Channel Specific Sampling Sequence (CSSS) is started. Typically CSSS sequences are applied on up to 3 of the most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference. The FS4 coding strategy differs from FSP in that up to 4 apical channels can have their fine structure information used. In FS4-p, stimulation pulse sequences can be delivered in parallel on any 2 of the 4 FSP electrode channels. With the FSP and FS4 coding strategies, the fine structure information is the instantaneous frequency information of a given electrode channel, which may provide users with an improved hearing sensation, better speech understanding and enhanced perceptual audio quality. See, e.g., U.S. Pat. No. 7,561,709; Lorens et al. "Fine structure processing improves speech perception as well as objective and subjective benefits in pediatric MED-EL COMBI 40+ users." *International journal of pediatric otorhinolaryngology* 74.12 (2010): 1372-1378; and Vermeire et al., "Better speech recognition in noise with the fine structure processing coding strategy." *ORL* 72.6 (2010): 305-311; all of which are incorporated herein by reference in their entireties.

Many cochlear implant coding strategies use what is referred to as an n-of-m approach where only some number n electrode channels with the greatest amplitude are stimulated in a given sampling time frame. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses. Thus, fewer electrode channels are available for coding important temporal and spectral properties of the sound signal such as speech onset.

In addition to the specific processing and coding approaches discussed above, different specific pulse stimulation modes are possible to deliver the stimulation pulses with specific electrodes—i.e. mono-polar, bi-polar, tri-polar, multi-polar, and phased-array stimulation. And there also are different stimulation pulse shapes—i.e. biphasic, symmetric triphasic, asymmetric triphasic pulses, or asymmetric pulse shapes. These various pulse stimulation modes and pulse shapes each provide different benefits; for example, higher tonotopic selectivity, smaller electrical thresholds, higher electric dynamic range, less unwanted side-effects such as facial nerve stimulation, etc.

Figure 2:
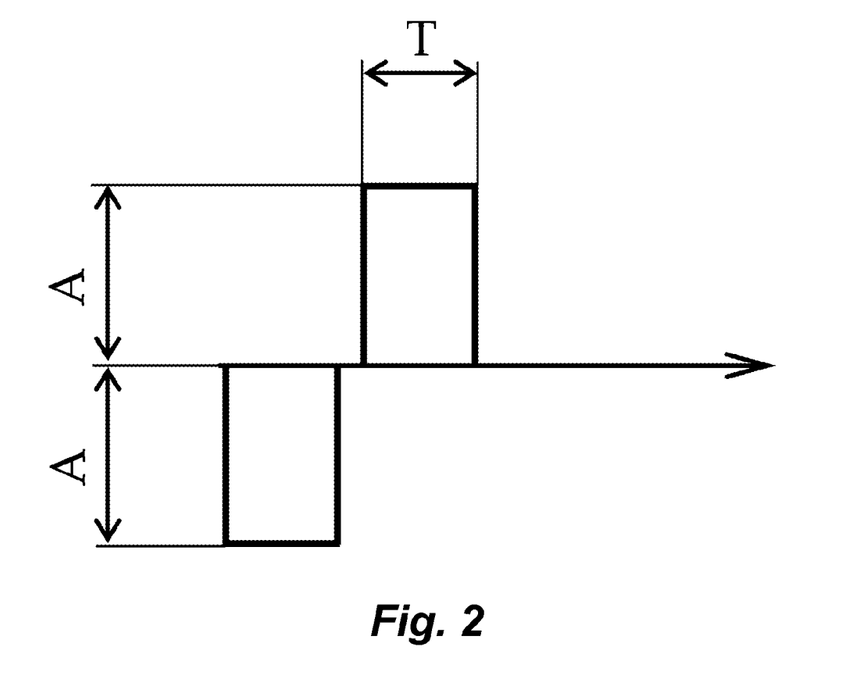
FIG. 2 shows an example waveform for a typical biphasic stimulation pulse.

The standard stimulation pulses in cochlear implants are biphasic. As shown in FIG. 2, such biphasic stimulation pulses have a negative half-wave (cathodic phase) and a charge-balanced positive half-wave (anodic phase). The net charge of a given half-wave pulse corresponds to the product of its current amplitude A and its pulse duration T. To ensure that no DC components are transmitted to the auditory nerve, the biphasic stimulation pulse includes an opposite phase half-wave pulse of equal duration and opposite amplitude to the first half-wave pulse. In specific pulsatile stimulation strategies, sequential or parallel pulses can be generated at different electrode contacts.

Sometimes, depending on the propagation of the electrical stimulation field and the specific anatomical situation, other nerves may be stimulated inadvertently. Such collateral stimulation can result in unintended somatic responses, which are side-effects such as twitching of the facial nerve and/or eye, or a burning sensation in the tongue or throat. These unpleasant somatic responses can increase in intensity with increasing charge. In some cases, this situation can prevent setting the stimulation intensity sufficiently high for effective hearing via the cochlear implant. If only one or a few electrode contacts are affected, these electrode contacts can be deactivated. But this change in the operation of the cochlear implant may have other undesirable consequences for the patient. If a considerable number of or all of the electrode contacts are affected, the cochlear implant may not be usable for hearing in extreme cases.

When setting the stimulation parameters in a patient fitting process, the fitting audiologist can try to change various stimulation parameters such as pulse width, stimulation rate and compression to provide a louder auditory sensation and reduce the undesired somatic responses. Re-implantation with a cochlear implant with a differently arranged reference electrode also has been attempted by placing separate ground electrodes at very specific locations. EP 0 959 943 mentions that facial nerve twitching can be an undesired somatic response. US 2012/0143284 also discusses the problem of undesirable facial nerve stimulation and other unwanted somatic responses. But throughout these documents this issue is always discussed in connection with extra-cochlear electrode contacts which are considered the source of these responses.

U.S. Pat. No. 5,601,617 describes selecting complex stimulus waveforms including triphasic stimulation pulses based on the "response" of the stimulated tissue. Generally the discussion assumes that this is the perceptive response and there is no mention of mitigating undesired somatic responses.

SUMMARY OF THE INVENTION

Embodiments of the present invention are directed to arrangements for generating electrode stimulation signals to electrode contacts in an implanted cochlear implant electrode array. A signal processor processes an input sound signal to generate stimulation timing signals for signal channels associated with the electrode contacts. A pulse generator produces the electrode stimulation signals for each electrode contact based on the stimulation timing signals. A pulse adapter controls a signal format of the pulse generator in response to a somatic response input signal reflecting presence or absence of an undesired somatic response to the electrode stimulation signals. When the somatic response input signal reflects absence of the undesired somatic response, then the signal format is an initial signal format based on biphasic stimulation pulses, and when the somatic response input signal reflects presence of the undesired somatic response, then the signal format is an adapted signal format based on triphasic stimulation pulses.

A variation of the adapted signal format includes charge-balanced triphasic stimulation pulses whereby gaps are introduced between the first and second, and between the second and third pulse phases. These gaps are designated as inter-phase-gaps and can range from 0 to several hundred microseconds, i.e. they are on the same order of magnitude than the individual pulse phase durations. The inter-phase gaps may be symmetric (equal duration) or asymmetric (unequal duration). Yet another variation of the adapted signal format includes charge-balanced biphasic stimulation pulses with one inter-phase gap between the first and second pulse phase. The duration of this inter-phase gap is on the same order of magnitude than the pulse phase durations.

The triphasic stimulation pulses may include first and third phase pulses matching each other in phase and opposite in phase to a second phase pulse. An alternative stimulation pulse for avoiding undesired somatic responses may be a biphasic stimulation pulse with a gap between the first and second pulse phase. The gap duration is on the order of magnitude of the pulse phase duration. All the phase pulses are equal in amplitude or duration. The first phase pulse may be anodic or cathodic. The triphasic stimulation pulses may be formed from consecutive biphasic pulses of opposite polarity. The adapted signal format may apply the stimulation pulses to the one or more electrode contacts sequentially to one electrode contact at a time, or in parallel to multiple electrode contacts at a time.

DETAILED DESCRIPTION OF SPECIFIC EMBODIMENTS

In addition to the typical biphasic stimulation pulses, most modern cochlear implants are capable of generating symmetrical triphasic stimulation pulses. But biphasic rather than triphasic pulses conventionally are used for cochlear implant stimulation in a normal operation mode, i.e. when the patient's auditory nerve is stimulated in order to provide auditory sensation. (The situation is different for the non-hearing situation of measuring nerve responses to stimulation pulses where it is known that triphasic stimulation pulses may favourably reduce stimulation artifacts.) No one in the field has identified any particular advantage to using triphasic stimulation pulses rather than biphasic stimulation pulses. In addition, if the individual pulse phases (positive and negative) become too short (e.g. shorter than about 10 μs), then a triphasic stimulation pulse that splits the duration of one of the pulse phases may lead to an uncertain charge balance because of the limited temporal resolution of the stimulation arrangement. That issue is not any sort of fundamental limit, but rather is a purely technical effect. Still there has been no reason to put any particular effort into reliable higher temporal resolution that could use much shorter pulse phases with a duration of just 2 or 3 μs while still reliably ensuring charge balance between the positive and negative pulse phases. Moreover, the overall maximum stimulation rate could be considerably decreased when using triphasic pulses.

So the potential use of triphasic stimulation pulses for cochlear implant systems has been mentioned before, but not thoroughly explored. And the problem of adverse side effects such as facial nerve stimulation, prickling in the cheeks, a sensation of stretching in the neck or twitching in the shoulder, has long been known. Similarly, a few patients also have reported having a metallic taste after having received a cochlear implant. This may occur after undesired stimulation of a gustative nerve. Furthermore, the inventors have observed that triphasic stimulation pulses as disclosed herein may be beneficial for patients having hypoplasia of the auditory nerve: "Hypoplasia of the auditory nerve (AN) refers to significant narrowing of the VIIIth cranial nerve which could compromise stimulation of the nerve by electrical pulses delivered from a cochlear implant (CI) [, . . . ]. To compensate, high current levels or increased charge may be required to elicit auditory perception causing current to spread to other cranial nerves and potentially resulting in unwanted myogenic responses." from Valero, Jerome, et al. "Electrophysiologic and behavioral outcomes of cochlear implantation in children with auditory nerve hypoplasia." *Ear and hearing* 33.1 (2012): 3-18; incorporated herein by reference in its entirety. But no one in the field has ever suggested that triphasic stimulation pulses might be used to prevent or mitigate such adverse and undesired somatic effects. But Applicant has determined that, in contrast to conventional biphasic stimulation pulses, triphasic stimulation pulses can significantly reduce undesired somatic responses while providing the desired loudness perception to the patient.

Thus, embodiments of the present invention are directed to arrangements for operating a cochlear implant system based on using triphasic stimulation pulses to avoid undesired somatic effects. Stimulation signals initially are applied to the electrode contacts based on an initial signal format that uses conventional biphasic stimulation pulses. But when one or more undesired somatic responses to the stimulation pulses are identified, such as facial nerve twitching, then an adapted signal format is selected that uses charge-balanced triphasic electrical stimulation pulses to apply stimulation signals to one or more of the electrode contacts, which can reduce the undesired somatic responses.

Figure 3:
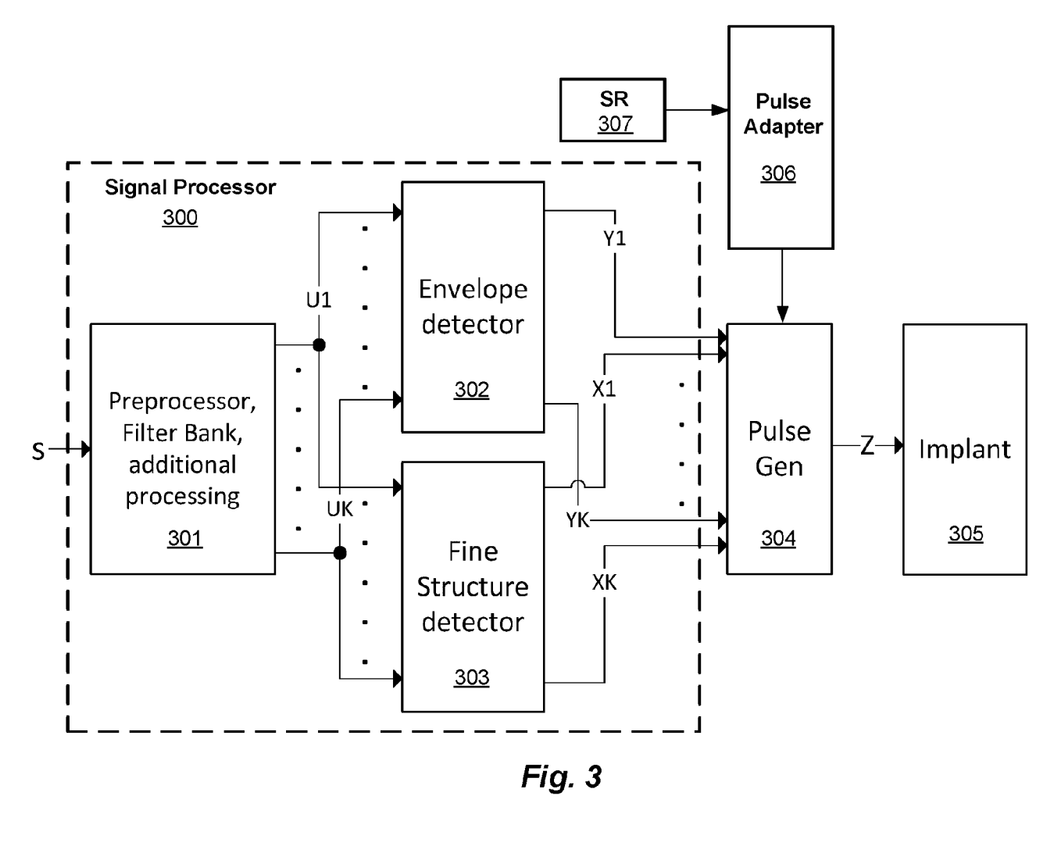
FIG. 3 shows various functional blocks in a signal processing arrangement for a hearing implant according to an embodiment of the present invention.
Figure 4:
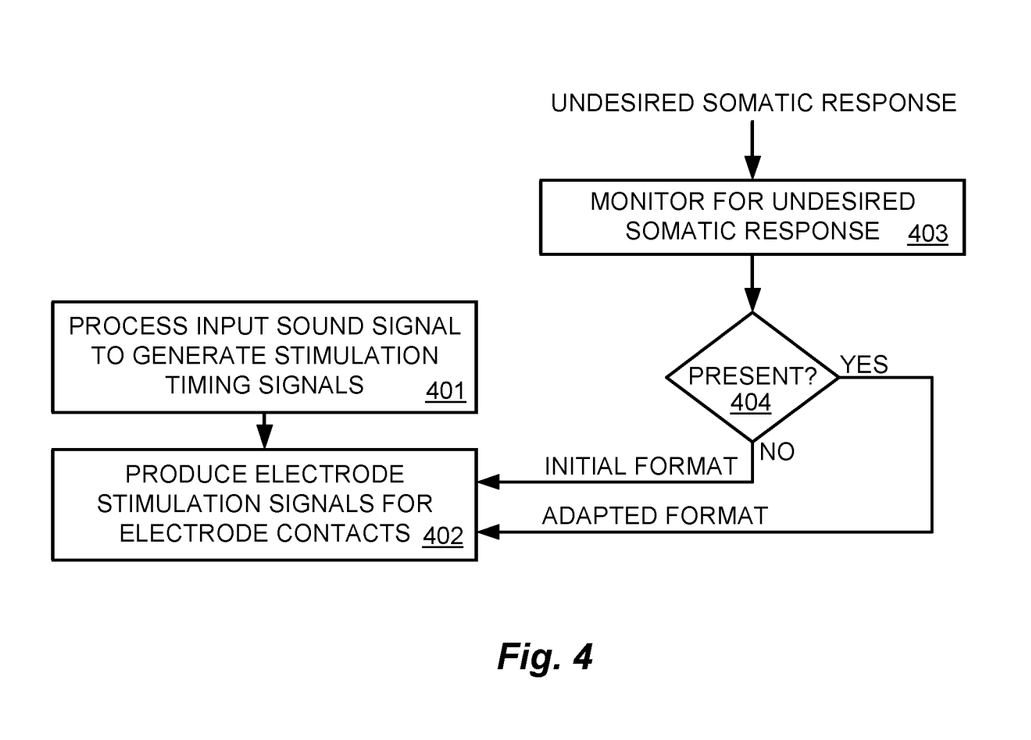
FIG. 4 shows various logical steps in developing electrode stimulation signals according to an embodiment of the present invention.

FIG. 3 shows various functional blocks in a signal processing arrangement for a hearing implant and FIG. 4 is a flow chart showing various logical steps in producing electrode stimulation signals to electrode contacts in an implanted cochlear implant array according to an embodiment of the present invention. A pseudo code example of such a method can be set forth as:

Sound Processing:
    SoundProcess (input_sound, stim_timing)
Pulse Generation:
    PulseGenerate (stim_timing, out_pulses)
Pulse Adaptation:
    PulseAdapt (out_pulses, som_response, sig_format)

The details of such an arrangement are set forth in the following discussion.

In the arrangement shown in FIG. 3, in which a Sound Processor 300 processes an input sound signal to generate stimulation timing signals for signal channels associated with the electrode contacts, step 401. More specifically, the initial input sound signal is produced by one or more sensing microphones, which may be omnidirectional and/or directional. Preprocessor Filter Bank 301 pre-processes the input sound signal with a bank of multiple parallel band pass filters (e.g. Infinite Impulse Response (IIR) or Finite Impulse Response (FIR)), each of which is associated with a specific band of audio frequencies; for example, using a filter bank with 12 digital Butterworth band pass filters of 6th order, Infinite Impulse Response (IIR) type, so that the acoustic audio signal is filtered into some K band pass signals, $U_1$ to $U_K$ where each signal corresponds to the band of frequencies for one of the band pass filters. Each output of sufficiently narrow CIS band pass filters for a voiced speech input signal may roughly be regarded as a sinusoid at the center frequency of the band pass filter which is modulated by the envelope signal. This is also due to the quality factor (Q≈3) of the filters. In case of a voiced speech segment, this envelope is approximately periodic, and the repetition rate is equal to the pitch frequency. Alternatively and without limitation, the Preprocessor Filter Bank 301 may be implemented based on use of a fast Fourier transform (FFT) or a short-time Fourier transform (STFT). Based on the tonotopic organization of the cochlea, each electrode contact in the scala tympani typically is associated with a specific band pass filter of the Preprocessor Filter Bank 301. The Preprocessor Filter Bank 301 also may perform other initial signal processing functions such as and without limitation automatic gain control (AGC) and/or noise reduction and/or wind noise reduction and/or beamforming and other well-known signal enhancement functions.

Figure 5:
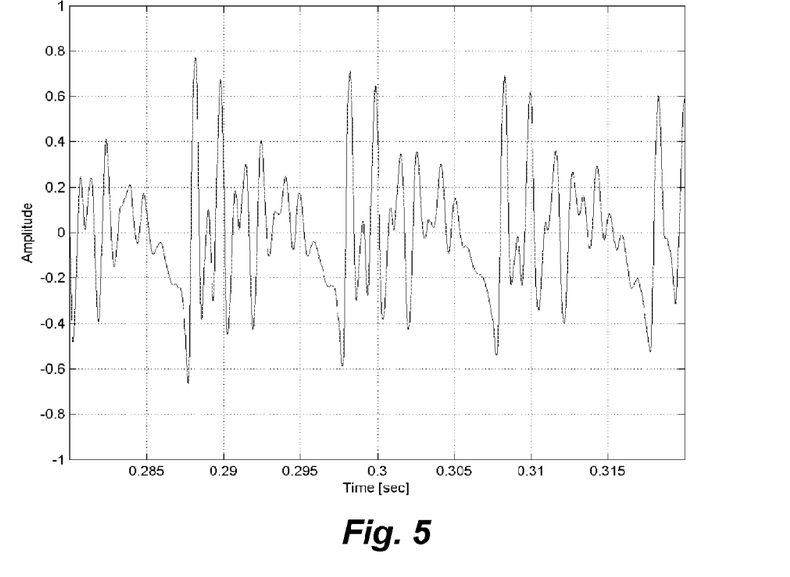
FIG. 5 shows an example of a short time period of an audio speech signal from a microphone.
Figure 6:
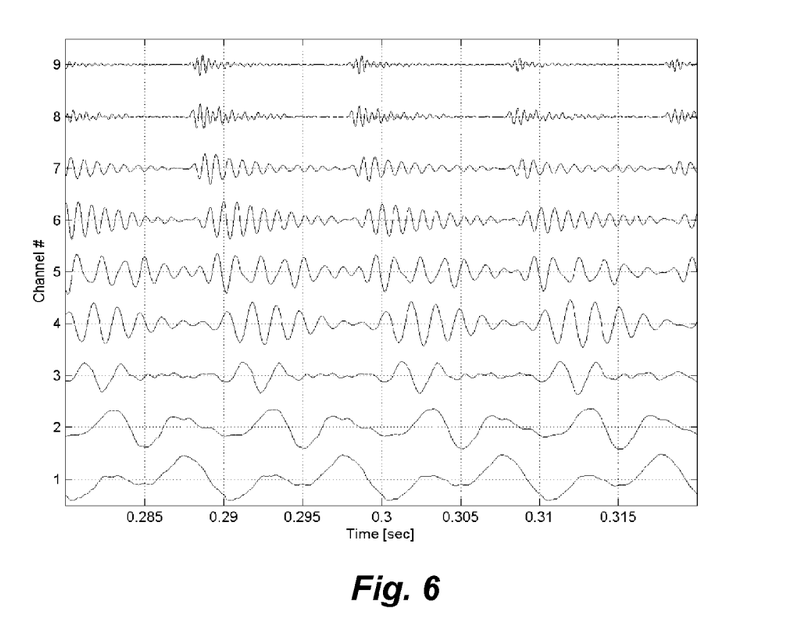
FIG. 6 shows an acoustic microphone signal decomposed by band-pass filtering by a bank of filters into a set of band pass signals.

FIG. 5 shows an example of a short time period of an input speech signal from a sensing microphone, and FIG. 6 shows the microphone signal decomposed by band-pass filtering by a bank of filters. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety.

The band pass signals $U_1$ to $U_K$ (which can also be thought of as electrode channels) are output by the Preprocessor Filter Bank 301 to an Envelope Detector 302 and Fine Structure Detector 303. The Envelope Detector 302 extracts characteristic envelope signals outputs $Y_1, \ldots, Y_K$, step 402, that represent the channel-specific band pass envelopes. The envelope extraction can be represented by $Y_k=LP(|U_k|)$, where |.| denotes the absolute value and LP(.) is a low-pass filter; for example, using 12 rectifiers and 12 digital Butterworth low pass filters of 2nd order, IIR-type. Alternatively, the Envelope Detector 302 may extract the Hilbert envelope, if the band pass signals $U_1, \ldots, U_K$ are generated by orthogonal filters.

The Fine Structure Detector 303 functions to obtain smooth and robust estimates of the instantaneous frequencies in the signal channels, processing selected temporal fine structure features of the band pass signals $U_1, \ldots, U_K$ to generate stimulation timing signals $X_1, \ldots, X_K$, step 403. In the following discussion, the band pass signals $U_1, \ldots, U_K$ are assumed to be real valued signals, so in the specific case of an analytic orthogonal filter bank, the Fine Structure Detector 303 considers only the real valued part of $U_k$. The Fine Structure Detector 303 is formed of K independent, equally-structured parallel sub-modules.

The extracted band-pass signal envelopes $Y_1, \ldots, Y_K$ from the Envelope Detector 302, and the stimulation timing signals $X_1, \ldots, X_K$ from the Fine Structure Detector 303 are input signals to a Pulse Generator 304 that produces the electrode stimulation signals Z for the electrode contacts in the electrode array of the Implant 305, step 402. The Pulse Generator 304 applies a patient-specific mapping function—for example, using instantaneous nonlinear compression of the envelope signal (map law)—That is adapted to the needs of the individual cochlear implant user during fitting of the implant in order to achieve natural loudness growth. The Pulse Generator 304 may apply logarithmic function with a form-factor C as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals. The electrode stimulation signals typically are a set of symmetrical biphasic current pulses.

Pulse Adapter 306 monitors a somatic response input signal, step 403, that reflects the presence or absence of an undesired somatic response (such as a facial nerve twitching) to the electrode stimulation signals in order to control a signal format of the Pulse Generator 304. For example, the somatic response input signal may be produced by an implanted sensor device 307, or it may be manually generated by the patient or by another observer such as a clinician. When the somatic response input signal reflects absence of the undesired somatic response, step 404, then the Pulse Adapter 306 selects an initial signal format for the Pulse Generator 304 that is based on biphasic stimulation pulses (see FIG. 2)

Figure 7:
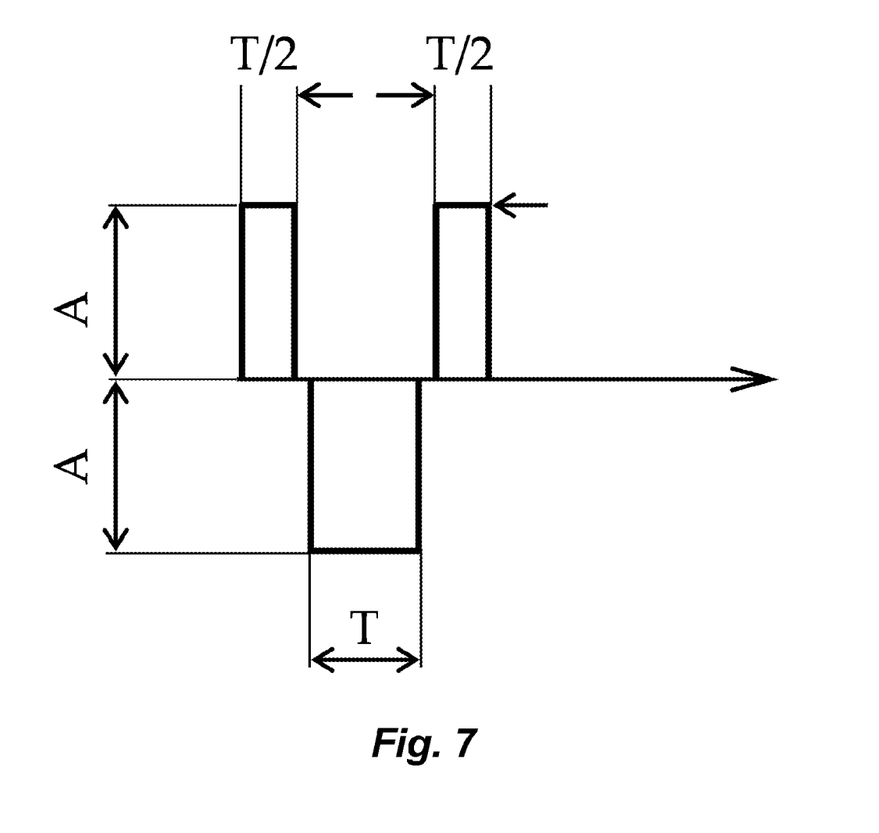
FIG. 7 shows an example waveform for one specific type of triphasic stimulation pulse according to an embodiment of the present invention where all the pulse phases have equal amplitudes and the first and third pulse phases are each half the duration of the second pulse phase.

When the somatic response input signal reflects the presence of the undesired somatic response, step 404, then the Pulse Adapter 306 selects an adapted signal format for the Pulse Generator 304 that is based on triphasic stimulation pulses. FIG. 7 shows an example waveform for one specific type of triphasic stimulation pulse according to an embodiment of the present invention where first and third phase pulses match each other in phase and are opposite in phase to a second phase pulse. In the waveform shown in FIG. 7, all the pulse phases have equal amplitude values with the first and third pulse phases each being half the duration of the opposite second pulse phase. In the waveform shown in FIG. 7, the first and third phase pulses are anodic (positive) and the second phase pulse is cathodic (negative). In other embodiments, it may be the reverse case. The adapted signal format may apply the stimulation pulses to the one or more electrode contacts sequentially to one electrode contact at a time, or in parallel to multiple electrode contacts at a time. The triphasic pulses may be applied to individual electrode contacts, to one or more sub-groups of electrode contacts, or to all the electrode contacts. They may be applied sequentially at different electrode contacts or in parallel.

Figure 8:
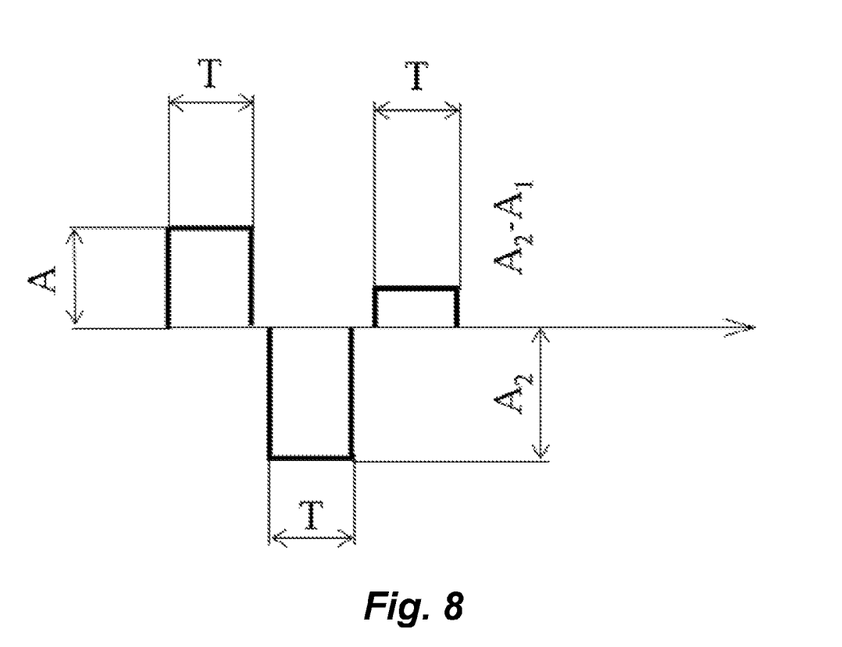
FIG. 8 shows an example waveform for another specific type of triphasic stimulation pulse according to another embodiment of the present invention where all the pulse phases have equal durations and the combined amplitudes of the first and third pulse phases are equal and opposite to the amplitude of the second pulse phase.

FIG. 8 shows an example waveform for another specific type of triphasic stimulation pulse according to another embodiment of the present invention using what are referred to as precision pulses. By that it is meant that all the pulse phases have equal durations and different amplitude values where the combined amplitudes of the first and third pulse phases are equal and opposite to the amplitude of the second pulse phase.

Figure 9:
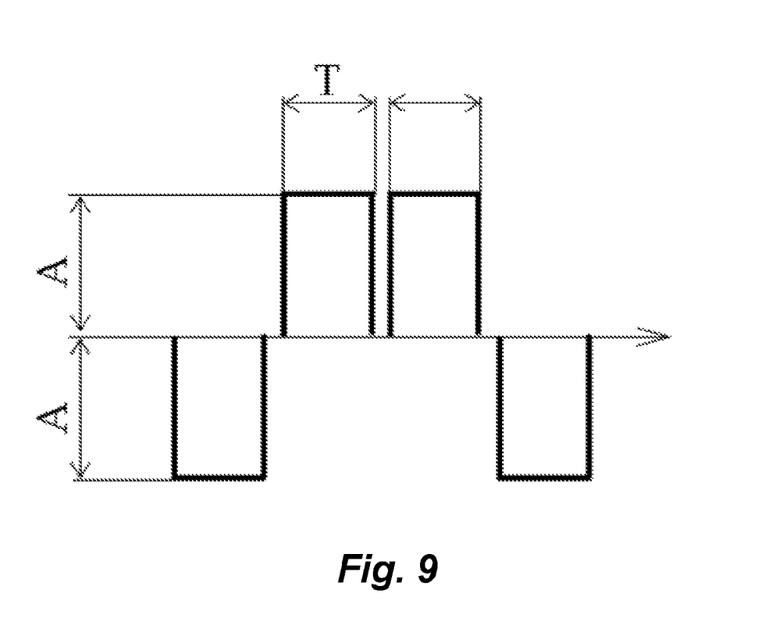
FIG. 9 shows an example waveform for another specific type of triphasic stimulation pulse according to another embodiment of the present invention based on back-to-back biphasic pulses of opposite phase.

FIG. 9 shows an example waveform for another specific type of triphasic stimulation pulse according to another embodiment of the present invention for systems which may not be capable of forming symmetrical triphasic stimulation pulses. In that case, triphasic pulses can be formed as shown based on back-to-back biphasic pulses of opposite phase.

Figure 10:
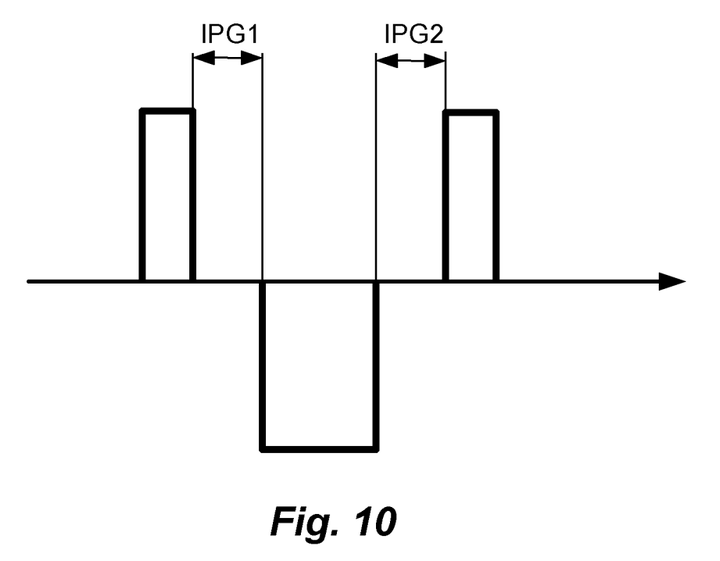
FIG. 10 shows an example waveform for another specific type of triphasic stimulation pulse according to another embodiment of the present invention based on inter-phase gaps between the first and second and between the second and third pulse phases.
Figure 11:
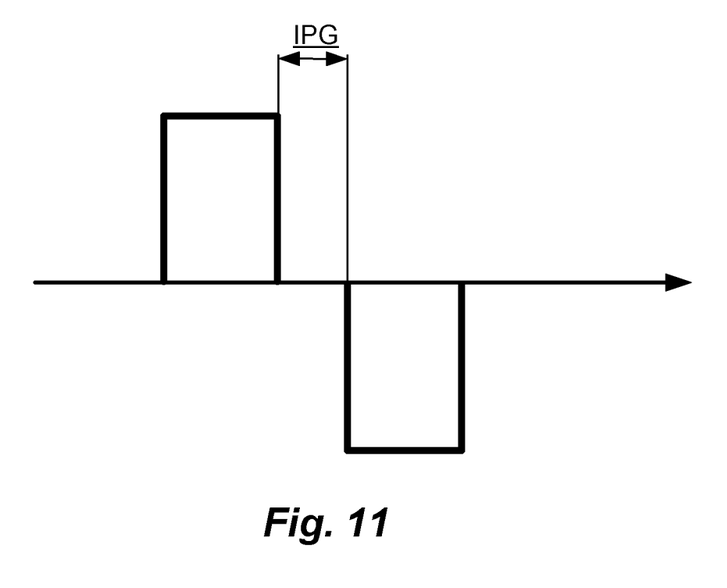
FIG. 11 shows an example waveform for another type of biphasic stimulation pulse according to another embodiment of the present invention based on an inter-phase gap between the first and second pulse phases.

FIG. 10 shows an example waveform for another specific type of triphasic stimulation pulse according to another embodiment of the present invention wherein the adapted signal format includes inter-phase gap periods between adjacent phase pulses; i.e., between the first and second ("IPG1"), and/or between the second and third pulse phases ("IPG2"). These inter-phase gaps IPG1 and IPG2 are on the same order of magnitude as the individual pulse phase durations, and so typically can range from zero to several hundred microseconds. In some specific embodiments, the inter-phase gaps may be variable in duration to adjust the one or more undesired somatic responses, and/or the inter-phase gaps may be symmetric (equal duration) or asymmetric (unequal duration). FIG. 11 shows an example waveform for another embodiment of the present invention based on a biphasic stimulation pulse with an inter-phase gap between the first and second pulse phases.

Applying triphasic pulses and keeping the pulse energy constant compared to the application of biphasic pulses usually result in a reduction of perceived loudness. Consequently, it may be necessary to increase the amount of charge per pulse phase. Increasing the phase amplitude only works until saturation effects of the nervous tissue occur. Increasing the phase lengths only works until the stimulation rate would not be decreased to an unacceptable value. Alternatively, parallel stimulation of two or more channels with or without using a channel interaction compensation (CIC) algorithms as e.g. disclosed in US2009/0036962. Such parallel stimulation with CIC may be also applied to a combination of bi- and triphasic pulses. Based on the foregoing, it is emphasized that the application of tri-phasic pulses may result in an increased stimulation energy in order to achieve the same perceived and, by the patient, demanded loudness level compared to using only biphasic stimulation pulses. It will be appreciated that the application of triphasic pulses may also be used not only in connection with monopolar but also bi-, tri- etc. stimulation modes.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A system for generating electrode stimulation signals to electrode contacts in an implanted cochlear implant electrode array, the system comprising:
   a signal processor configured to process an input sound signal to generate a plurality of stimulation timing signals associated with the electrode contacts;
   a pulse generator using a stimulation signal format and configured to produce the electrode stimulation signals for each electrode contact based on the stimulation timing signals;
   a somatic response sensor configured to generate a somatic response signal identifying presence and absence of an undesired somatic response due to the electrode stimulation signals inadvertently stimulating a non-targeted nerve; and
   a pulse adapter configured to control the stimulation signal format of the pulse generator in response to the somatic response signal, wherein:
   i. the stimulation signal format is an initial signal format with electrode stimulation signals having biphasic stimulation pulses when the somatic response signal reflects absence of the undesired somatic response, and
   ii. the stimulation signal format is an adapted signal format with electrode stimulation signals having triphasic stimulation pulses when the somatic response signal reflects presence of the undesired somatic response.

2. The system according to claim 1, wherein the triphasic stimulation pulses include first and third phase pulses matching each other in phase and opposite in phase to a second phase pulse.

3. The system according to claim 2, wherein all the phase pulses are equal in amplitude.

4. The system according to claim 2, wherein all the phase pulses are equal in duration.

5. The system according to claim 2, wherein the adapted signal format includes one or more inter-phase gap periods between adjacent phase pulses.

6. The system according to claim 5, wherein the one or more inter-phase gap periods are variable in duration to adjust the one or more undesired somatic responses.

7. The system according to claim 1, wherein the adapted signal format applies the stimulation pulses to the electrode contacts sequentially to one electrode contact at a time.

8. The system according to claim 1, wherein the adapted signal format applies the stimulation pulses to the electrode contacts in parallel to multiple electrode contacts at a time.

9. A computer program product encoded in a non-transitory computer-readable medium for generating electrode stimulation signals to electrode contacts in an implanted cochlear implant electrode array, the product comprising:
   program code for processing an input sound signal to generate a plurality of stimulation timing signals associated with the electrode contacts;
   program code for using a stimulation signal format to produce the electrode stimulation signals for each electrode contact based on the stimulation timing signals;
   program code for generating a somatic response signal identifying presence and absence of an undesired somatic response due to the electrode stimulation signals inadvertently stimulating a non-targeted nerve; and
   program code for controlling the stimulation signal format of the electrode stimulation signals based on the somatic response signal, wherein:
      i. the stimulation signal format is an initial signal format with electrode stimulation signals having biphasic stimulation pulses when the somatic response signal reflects that the undesired somatic response is absent, and
      ii. the stimulation signal format is an adapted signal format with electrode stimulation signals having triphasic stimulation pulses when the somatic response signal reflects that the undesired somatic response is present.

10. The product according to claim 9, wherein the triphasic stimulation pulses include first and third phase pulses matching each other in phase and opposite in phase to a second phase pulse.

11. The product according to claim 10, wherein all the phase pulses are equal in amplitude.

12. The product according to claim 10, wherein all the phase pulses are equal in duration.

13. The product according to claim 10, wherein the adapted signal format includes one or more inter-phase gap periods between adjacent phase pulses.

14. The product according to claim 13, wherein the one or more inter-phase gap periods are variable in duration to adjust the undesired somatic response.

15. The product according to claim 9, wherein the adapted signal format applies the stimulation pulses to the electrode contact sequentially to one electrode contact at a time.

16. The product according to claim 9, wherein the adapted signal format applies the stimulation pulses to the electrode contacts in parallel to multiple electrode contacts at a time.

17. A method of generating electrode stimulation signals to electrode contacts in an implanted cochlear implant electrode array, the method comprising:
   processing an input sound signal to generate a plurality of stimulation timing signals associated with the electrode contacts;
   using a stimulation signal format to produce the electrode stimulation signals for each electrode contact based on the stimulation timing signals;
   generating a somatic response signal identifying presence and absence of an undesired somatic response due to the electrode stimulation signals inadvertently stimulating a non-targeted nerve; and
   controlling the stimulation signal format of the electrode stimulation signals based on the somatic response signal, wherein:
      i. the stimulation signal format is an initial signal format with electrode stimulation signals having biphasic stimulation pulses when the somatic response signal reflects that the undesired somatic response is absent, and
      ii. the stimulation signal format is an adapted signal format with electrode stimulation signals having triphasic stimulation pulses when the somatic response signal reflects that the undesired somatic response is present.

18. The method according to claim 17, wherein the triphasic stimulation pulses include first and third phase pulses matching each other in phase and opposite in phase to a second phase pulse.

19. The method according to claim 18, wherein all the phase pulses are equal in amplitude.

20. The method according to claim 18, wherein all the phase pulses are equal in duration.

21. The method according to claim 18, wherein the adapted signal format includes one or more inter-phase gap periods between adjacent phase pulses.

22. The method according to claim 21, wherein the one or more inter-phase gap periods are variable in duration to adjust the undesired somatic response.

23. The method according to claim 17, wherein the adapted signal format applies the stimulation pulses to the electrode contact sequentially to one electrode contact at a time.

24. The method according to claim 17, wherein the adapted signal format applies the stimulation pulses to the electrode contacts in parallel to multiple electrode contacts at a time.

* * * * *